(12) United States Patent
Lampotang et al.

(10) Patent No.: US 6,370,419 B2
(45) Date of Patent: Apr. 9, 2002

(54) METHOD AND APPARATUS FOR TRIGGERING AN EVENT AT A DESIRED POINT IN THE BREATHING CYCLE

(75) Inventors: Samsun Lampotang; Paul B. Langevin, both of Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/026,908

(22) Filed: Feb. 20, 1998

(51) Int. Cl.$^7$ .................................................. A61B 5/00
(52) U.S. Cl. ...................... 600/427; 600/428; 600/538; 600/539; 378/95; 128/202.13; 128/202.16
(58) Field of Search ................................ 600/411, 413, 600/427, 428, 529, 534, 538, 539; 128/200.24, 202.13, 202.16; 378/98, 95, 117, 147

(56) References Cited

U.S. PATENT DOCUMENTS

| | | | |
|---|---|---|---|
| 3,871,360 A | | 3/1975 | Van Horn et al. |
| 3,993,995 A | * | 11/1976 | Kaplan et al. ............... 600/428 |
| 4,123,654 A | | 10/1978 | Reiss et al. |
| 4,387,722 A | * | 6/1983 | Kearns ........................ 600/529 |
| 4,991,193 A | * | 2/1991 | Cecil et al. .................. 378/117 |
| 4,994,744 A | | 2/1991 | Glover et al. |
| 5,018,178 A | * | 5/1991 | Katsumata ................... 378/91 |
| 5,067,494 A | * | 11/1991 | Rienmueller et al. ....... 600/428 |
| 5,485,833 A | | 1/1996 | Dietz |
| 5,485,835 A | | 1/1996 | Vande Streek et al. |
| 5,870,450 A | * | 2/1999 | Khutoryansky et al. .... 378/197 |
| 6,099,481 A | * | 8/2000 | Daniels et al. .............. 600/538 |

FOREIGN PATENT DOCUMENTS

| | | |
|---|---|---|
| DE | 0377764 | 12/1989 |
| FR | 2604890 | 10/1986 |
| JP | 07210247 | 7/1995 |

OTHER PUBLICATIONS

Ehman et al. (1994) "Magnetic Resonance Imaging with Respiratory Gating: Techniques and Advantages" AJR:143.

* cited by examiner

*Primary Examiner*—Ruth S. Smith
(74) *Attorney, Agent, or Firm*—Saliwanchik, Lloyd & Saliwanchik

(57) ABSTRACT

The subject invention pertains to a novel method and apparatus for improving the efficacy of a medical treatment or diagnostic procedure by coordinating such treatment or procedure with a patient's breathing cycle. In a specific embodiment, the subject invention pertains to a novel method of coordinating a chest x-ray with a patient's ventilatory cycle. In a specific example, this invention concerns a novel device for interfacing a ventilator and an x-ray machine to ensure that an x-ray chest image can be taken at peak insufflation of the patient. The subject invention also relates to other medical procedures including, but not limited to, cardiac output measurement, chest imaging, inhalation therapy, oxygen delivery, blood pressure measurement, and pulse oximeter optoplethysmograms. By coordinating certain medical treatments and diagnostic procedures with a patient's breathing cycle, the subject invention improves the quality of medical care received by the patient.

23 Claims, 5 Drawing Sheets

METHOD AND APPARATUS FOR TRIGGERING AN EVENT AT A DESIRED POINT IN THE BREATHING CYCLE

BACKGROUND OF THE INVENTION

There are many medical treatments and diagnostic procedures the efficacy of which can be improved by coordinating such treatment or procedure with a patient's breathing cycle. In many instances the patient can control their breathing to assist the medical provider. However, some patients are not able to control their breathing, for example patients on ventilators. Accordingly, an apparatus which could facilitate the timing of such a medical treatment or a diagnostic procedure with respect to a patient's breathing cycle would be beneficial to the patient.

As an example, chest x-rays are often taken in the intensive care unit using portable x-ray machines. These x-ray images provide important information to the clinician and, therefore, the quality of the images is important. Factors which can affect the quality of chest x-rays include: patient position and movement; ability of patient to receive and respond to instruction; penetration of the x-ray beam; and, perhaps most important, timing of the x-ray with patient insufflation.

Typically, the highest quality chest x-ray images are attained when the x-ray is taken at peak insufflation because there is less tissue mass per unit area, and penetration is uniform. Accordingly, patients who are able to receive and respond to instruction can be instructed to take and hold a deep breath long enough to take the required x-rays. However, for patients on a ventilator, in order to take the x-ray at peak insufflation, the person taking the x-ray must attempt to accurately time the x-ray with the cycle of the ventilator. When the x-ray is not timed correctly, it may be less than optimal and additional costs are incurred if it is necessary to retake the x-rays. Furthermore if time is critical, the care giver may be forced to provide care with inadequate information.

Accordingly, there exists a need in the art for a method and device which can ensure that chest images of patients on ventilators are taken at a desired degree of insufflation to enhance the quality of such chest images. In particular, a device which could interface a ventilator with an x-ray machine to ensure chest x-rays are taken at peak ventilation would improve the quality of such chest x-rays and, therefore, improve the quality of care for ventilated patients.

Additional situations where the efficacy of the medical treatment or procedure can be affected by timing the treatment or procedure with respect to a desired point in the breathing cycle include, but are not limited to, inhalation therapy, oxygen ($O_2$) delivery, blood pressure measurements, and pulse oximeter optoplethysmograms. With inhalation therapy and $O_2$ delivery, timing the delivery of the appropriate substances with respect to the breathing cycle can affect the dose administered, the amount of waste, and costs. With blood pressure measurements and pulse oximeter optoplethysmograms, the timing of the measurements with respect to the breathing cycle can affect, for example, the accuracy of the readings.

Accordingly, there exists a need in the art for a method and device which can trigger an event with respect to a patient's breathing cycle.

BRIEF SUMMARY OF THE INVENTION

The subject invention pertains to a method and apparatus for triggering an event with respect to a patient's breathing cycle. The subject invention is applicable to human or animal patients. In a specific embodiment, the subject invention pertains to a novel method of coordinating a chest x-ray with the ventilatory cycle. The methods and apparatus of the subject invention are particularly advantageous for use in chest radiography. In a specific example, the subject invention concerns a novel device for interfacing a ventilator and an x-ray machine to ensure that an x-ray chest image can be taken at a desired degree of ventilation of the patient, for example, peak inspiration. The interfacing of a ventilator and an x-ray machine, according to the subject invention improves the chest image quality and, therefore, improves the quality of medical care received by the patient. In a preferred embodiment, the taking of an x-ray can be accomplished by emulating an x-ray machine firing handle with software, for example, on a notebook personal computer.

Further embodiments of the subject invention pertain to, for example, the delivery of inhalants, delivery of oxygen ($O_2$), blood pressure measurements, and pulse oximeter optoplethysgrams. With respect to the delivery of inhalants and the delivery of $O_2$, the method and apparatus of the subject invention can improve the efficiency of the delivery of the appropriate substance, improve the accuracy of administering the correct dose, and reduce waste and costs. With respect to blood pressure measurements and pulse oximeter optoplethysgrams, the method and apparatus of the subject invention can improve the clarity of the film increasing the accuracy of the films' interpretation by timing the measurements with respect to the breathing cycle of a patient.

DETAILED DESCRIPTION OF THE INVENTION

The subject invention pertains to a method and apparatus for coordinating, for example triggering, an event, for example, a medical treatment or a diagnostic procedure, with respect to a patient's breathing cycle. In particular, patients on a ventilator can benefit from the subject invention.

In a specific embodiment, the subject invention pertains to a novel method for timing a chest image with the ventilatory cycle. The subject method and apparatus can ensure images of the chest are taken at a desired degree of insufflation of the patient and, therefore, improve the quality of such chest images. In a specific embodiment, this invention concerns a novel device for interfacing a ventilator and an x-ray machine, to ensure that an x-ray chest image can be taken at peak ventilation of a patient and thereby enhances the quality of such an x-ray chest image.

Figure 1:
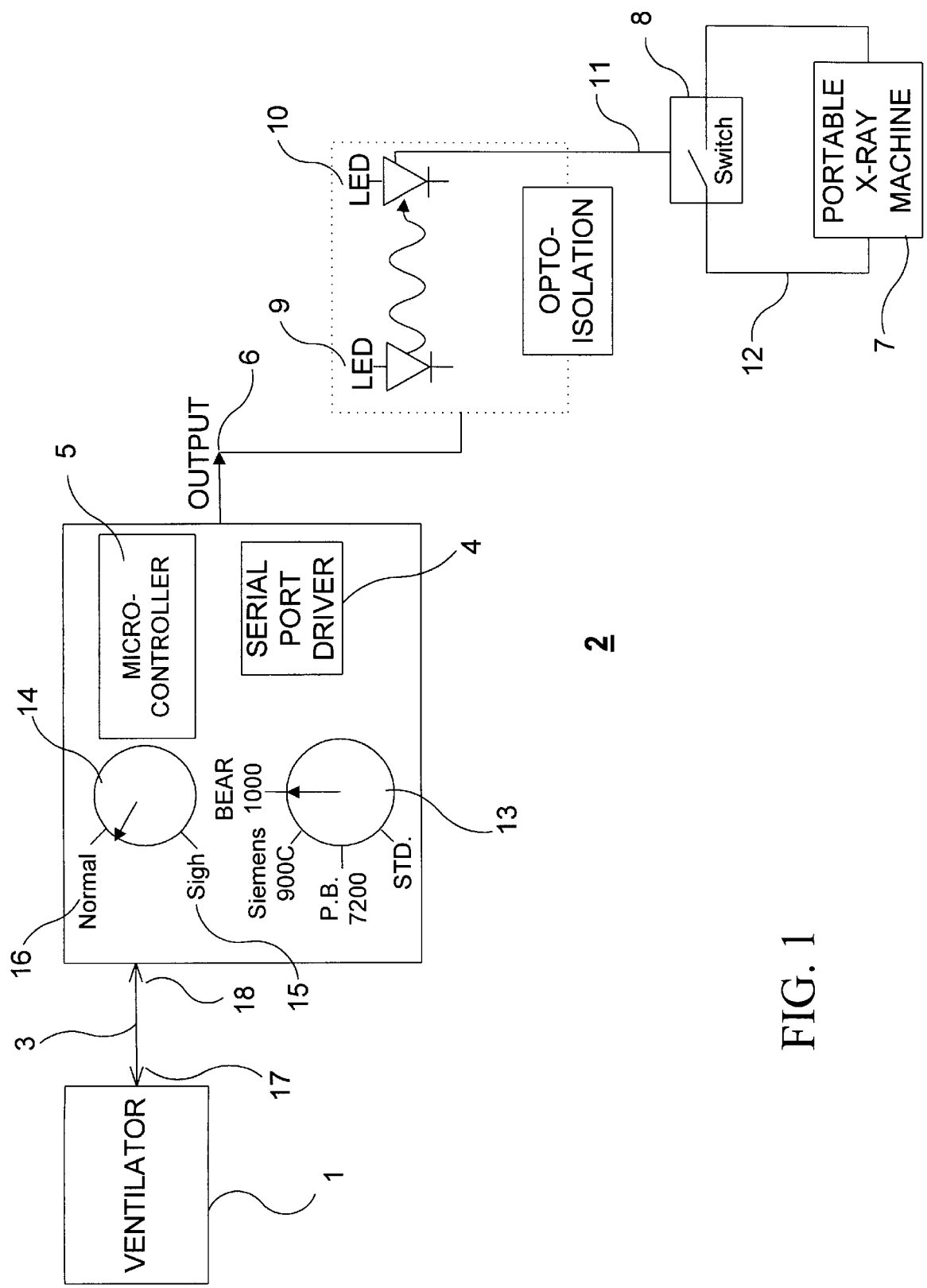
FIG. 1 shows a block diagram of an embodiment of an apparatus to interface a ventilator and an x-ray machine wherein a signal from the ventilator is utilized, in accordance with the subject invention.

Referring to FIG. 1, a block diagram of an apparatus for interfacing a ventilator and an x-ray machine is shown in accordance with the subject invention. Ventilator 1 can retrieve and send data to interface 2 on, for example, a serial communication link 3. A first end 17 of serial communication link 3 can connect to the ventilator, for example to the serial port (RS-232) of the ventilator, and a second end 18 of serial communication link 3 can connect to the interface 2, for example to a serial port driver 4. Serial port driver 4 can be linked to microcontroller 5. Microcontroller 5 can have an output 6 to, for example, an x-ray machine 7. In a specific embodiment, output 6 can be connected to a switch 8, where upon receiving an appropriate signal switch 8 closes, effecting the taking of an x-ray.

In order to minimize the risk of injury to the patient, the subject invention can provide a means for isolating ventilator 1 and interface 2 from the electrical circuitry of x-ray machine 7. This isolation means can include, for example, RF circuitry, IR detectors, LED's, lasers, photodetectors, or other appropriate devices which can send and receive a signal without a direct wire connection. In a preferred embodiment, output 6 can be connected to first LED 9, where upon first LED 9 receiving an appropriate signal from interface 2, first LED 9 can send a light signal to second LED 10 which can then send an appropriate signal 11 to, for example, portable x-ray machine 7. First LED 9 and second LED 10 used in this way act to isolate ventilator 1 and interface 2 from the electrical circuitry of x-ray machine 7. This isolation, referred to as opto-isolation, isolates the patient from the electrical circuitry of x-ray machine 7 and, therefore, improves patient safety. In a specific embodiment, the output signal 11 from second LED 10 can be sent to switch 8 which then switches x-ray machine 7 on and off, for example via cable 12. In addition, cable 12 can, for example, be connected to a toggle switch on an x-ray machine which is typically operated, manually, by the x-ray technician.

The subject invention allows microcontroller 5, having access to the status of ventilator 1, to effect the taking of a chest image by sending an appropriate output signal 6 to, for example, an x-ray machine. In a preferred embodiment, microcontroller 5 can be connected to a ventilator model selector switch 13, for example a manual switch on the interface, which can have settings corresponding to existing ventilator models. These ventilator models can include, for example, Siemens 900C, P.B. 7200, BEAR 1000, and STD. By setting switch 13 to a particular model, microcontrollers can monitor signals from ventilator 1 corresponding to the status of ventilator 1 and effect the taking of an x-ray at a desired degree of ventilation of the patient, for example at peak ventilation.

For patients who are able to receive a sigh breath, in order to realize peak ventilation it is preferred to take a chest x-ray during a sigh breath. A sigh breath has approximately three times the tidal volume as a normal breath and, therefore, taking a chest x-ray during a sigh breath improves the quality of the resulting chest x-ray. However, some patients are unable to receive a sigh breath because of medical reasons. In a preferred embodiment, interface 2 can have a sigh switch 14 which, when set to sigh 15, enables microcontroller 5 to signal ventilator 1 to administer to the patient a sigh breath and, subsequently, effect the taking of an x-ray during the sigh breath. When sigh switch 14 is set to normal 16, the patient is not given a sigh breath and an x-ray can be taken at a desired degree of ventilation, for example at peak insufflation for a regular tidal volume breath.

In an additional embodiment, interface 2 can have a switch which indicates the degree of insufflation of the patient at which a chest image is to be taken. This switch can allow a chest image to be taken at, for example, minimum insufflation of the patient. Accordingly, the subject invention can enable a comparison of a chest image at minimal insufflation and a chest image at maximum insufflation. This switch can have settings of, for example, minimum, 25% maximum, 50% maximum, and maximum insufflation. To coordinate with sigh switch 14, the switch which indicates the degree of insufflation can also have a sigh setting for use when a sigh breath is desired.

In a further embodiment, interface 2 can have a setting, for example on the ventilator model selector switch 13, for patients who are spontaneously breathing and, therefore, are not on a ventilator. Alternatively, interface 2 can have an override switch for patients who are not on a ventilator. For a patient who is spontaneously breathing, interface 2 can receive a signal from a means for determining the degree of insufflation of a patient. Thereby, interface 2 can effect the taking of a chest image at peak insufflation, even for a patient who is spontaneously breathing and, therefore, not on a ventilator.

Further embodiments of the subject invention can enable the capture or identification of any given point in the breathing cycle, for example a desired phase of a breath, using either a ventilator, a flowmeter position either at the Y-piece or at the ventilator-inspiratory hose connection, or any monitor or instrument that allows positive identification of a point in the breathing cycle. Accordingly, events can be triggered to occur at any desired point in the breathing cycle. The instrument or monitor for identifying a point in the breathing cycle can be, for example, a Propaq portable monitor, a Hewlett Packard Merlin, or a Datex AS/3.

Figure 2A:
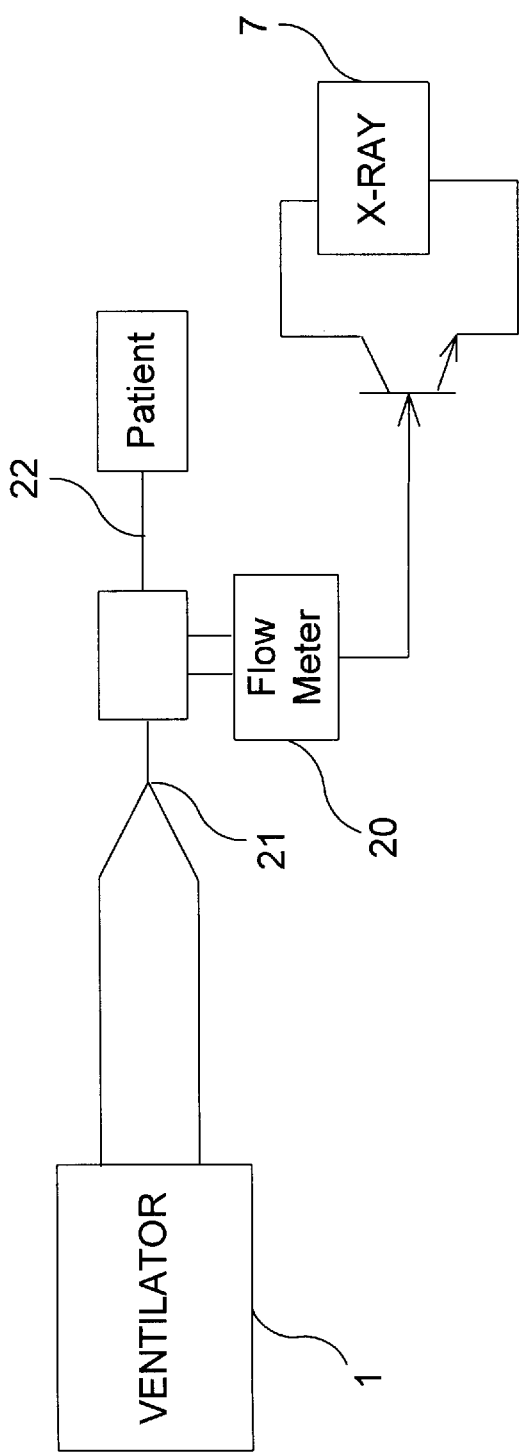
FIG. 2A shows a block diagram of an embodiment of an apparatus to interface a ventilator and an x-ray machine wherein a flowmeter positioned at the Y-branch is utilized, in accordance with the subject invention.

Referring to FIG. 2A, in a specific embodiment of the subject invention, instead of an electronic signal from a ventilator being utilized to detect the degree of a patient's insufflation, a flowmeter 20, for example placed at a patients Y-piece 21, can be used to detect the degree of insufflation. Advantageously, the use of flowmeter 20 allows the degree of insufflation to be determined even when using an entirely pneumatic ventilator. Accordingly, the use of flowmeter 20 allows an x-ray machine 7 to be triggered from any ventilator, electronic or pneumatic. A specific flowmeter which can be utilized according to the subject invention is a Norametrix flowmeter. In a specific embodiment, the flowmeter probe can be left in the circuit, between the breathing circuit Y-piece 21 and the end tracheal tube 22, at all times, thus eliminating the necessity of inserting and removing the flowmeter each time an x-ray is taken.

Figure 2B:
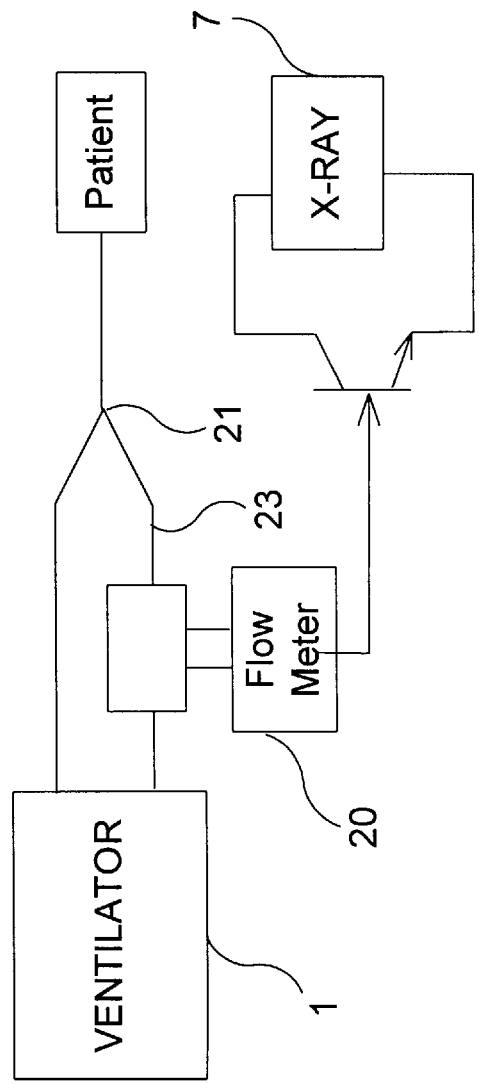
FIG. 2B shows a block diagram of an embodiment of an apparatus to interface a ventilator and an x-ray machine wherein a flowmeter positioned at the ventilator-respiratory hose connection is utilized, in accordance with the subject invention.

In a preferred embodiment, flowmeter 20 can be placed inside ventilator 1, reducing the risk of damage or user misuse. However, referring to FIG. 2B, if flowmeter 20 is moved to either respiratory port/hose connection 23 or the inside of ventilator 1, the zero flow crossing may not be as clearly defined as when flowmeter 20 is placed at Y-piece 21. In this case, the algorithm can be changed to a predictive one, where the cycle time of each breath is estimated, for example, by measuring the time between two peak inflations. Accordingly, the next peak inflation is predicted based on the cycle time. The efficacy of this method is optimum when the cycle time is regular, which is often the case for mechanical ventilation.

In an additional embodiment of the subject invention, a cardiac output curve can be shot off a precise trigger from a ventilator breath. A cardiac output curve indicates the amount of blood the heart is pumping per minute. One method for producing a cardiac output curve is by cardiac thermo-dilution wherein one injects a cold fluid into an artery, for example at point A, near the output of the heart and then monitors the temperature of the fluid passing through the arterial system, for example at point B, further away from the heart than point A where the cold fluid was injected. A temperature versus time curve taken at point B can provide information which can indicate the cardiac output of the patient. By triggering the cardiac output curve with the breathing cycle of the patient, the accuracy of the determination of the cardiac output can be enhanced. The subject invention can be utilized to perform cardiac output curves for patients on a ventilator and for patients not on a ventilator.

Additional embodiments of the subject invention can be utilized to trigger an event, for example, inhalation therapy, at some desired point in the breathing cycle, for example, peak inflation, pause, expiration, etc. In a specific embodiment, the inhalation therapy can relate to aerosols, for example albuterol. Similarly, the system can also be used in $O_2$ conservers. For example, $O_2$ can be delivered only during inhalation which can conserve $O_2$ because $O_2$ is not delivered during exhalation. The delivery of aerosol inhalants into the pulmonary tree can be improved by timing the delivery with respect to a ventilator breath, because the flow passages are fully opened at peak inflation and the aerosol molecules can therefore reach further into the pulmonary tree. Accordingly, it might be preferred to start the aerosol delivery at the beginning of inhalation rather than the end of inhalation. Alternatively, it might be preferred to have the delivery of the aerosol occur during the entire inhalation period, i.e., the flow of gas from the ventilator acts as an additional propellant for the aerosol helping the aerosol molecules reach deeper within the lungs. It might be preferred to start the delivery of the aerosol midway or partway in the process of inhalation. Conversely, one can stop aerosol therapy, especially for expensive aerosols, during exhalation as the flow of gases away from the patent's lungs will tend to drive the aerosol molecules away from the lungs, thus preventing waste of expensive aerosol. In any of these cases, triggering the aerosol delivery to specific parts of the breathing cycle can be beneficial.

Figure 3:
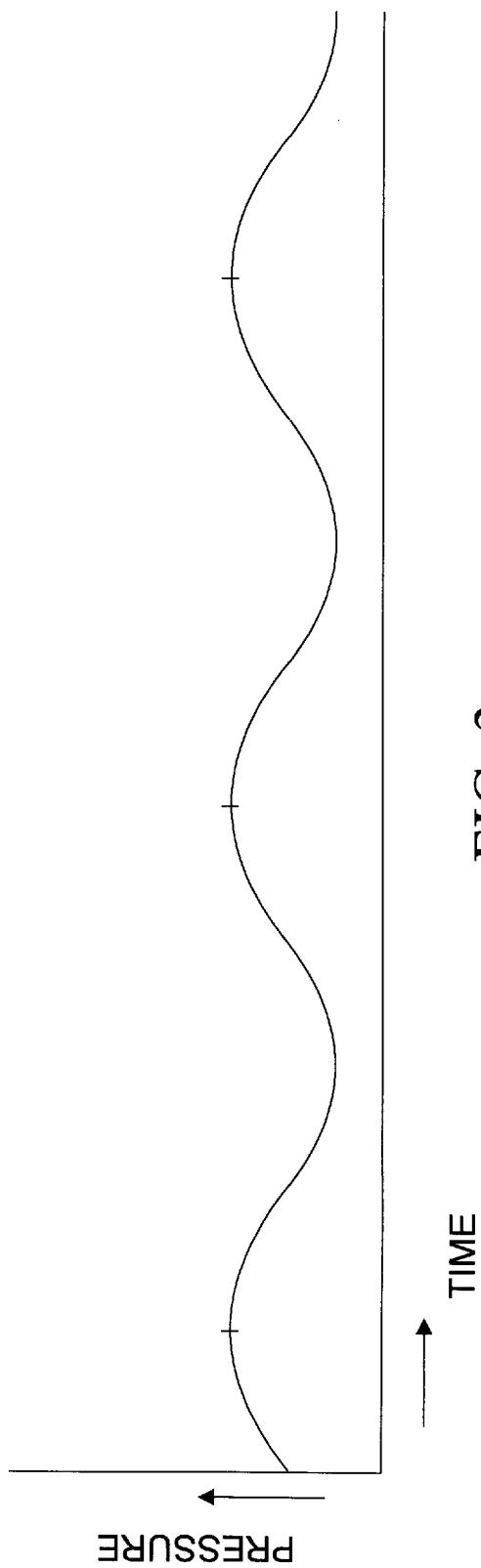
FIG. 3 illustrates the variation of the central venous pressure as a function of time due to the effect of respiration.

The subject invention can also be utilized to remove respiratory artifacts from signals affected by the respiratory cycle. For example, it is well known that respiration introduces artifacts in the measurement of blood pressure, for example, the central venous pressure or arterial pressure, or the pulse oximeter optoplethysmograms. FIG. 3 illustrates roughly the variation in the central venous pressure as a function of time due to the effect of respiration. Ventilators are often turned off during certain measurements in order to eliminate the respiratory artifact. The subject invention can allow the measurement to be taken without turning the ventilator off, thus improving patient safety, and allowing for continuous monitoring. By timing a measurement to be taken at the same point of each breath, the respiratory artifact can be eliminated and measurements are more consistent. For example, the effect of respiration on central venous pressure (CVP) or pulmonary artery pressure (PAP) are very pronounced. By timing the measurement to occur at the start of inhalation, the respiratory artifact can be reduced. Advantageously, in accordance with the subject invention, a CVP measurement can always be taken at the same point in the breath cycle. Therefore, the CVP trace or measurement is steadier.

Current portable x-ray machines, for example the General Electric model GEAMX4, utilize a firing handle to facilitate the taking of an x-ray. On a typical firing handle, a first switch can turn on a collimator light used for aiming the x-ray machine. A second switch, for example a button, can "arm" the x-ray machine and charge the capacitors that power the x-ray, referred to as "rotor-up." Finally, a third switch, for example a button, can discharge the capacitors producing the x-ray beam. There is usually a delay between pressing the "rotor-up" button and the "fire" button because it can take some time for the capacitors to charge.

Figure 6:
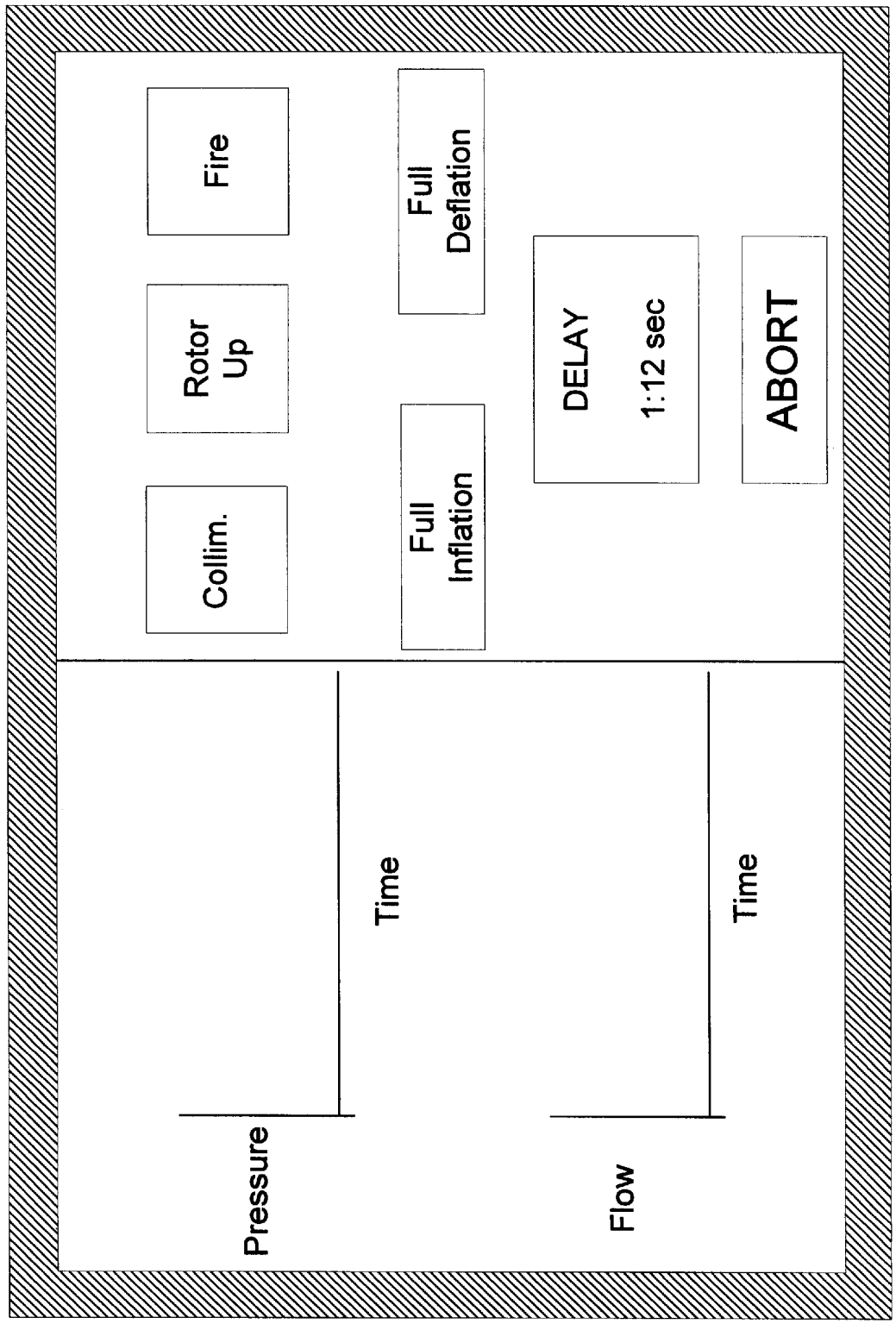
FIG. 6 illustrates an embodiment of a computer screen display in accordance with the subject invention.

In a specific embodiment of the subject invention, the firing of an x-ray is accomplished with a "fire" button on a user interface, for example implemented graphically on a notebook personal computer (PC) as shown in FIG. 6. For example, when an operator clicks on the "fire" button with the mouse, the "rotor-up" switch equivalent, for example a transistor, can be closed. There can be a fixed delay (e.g., 2 seconds) between the transistor representing the "rotor-up" switch closing and the algorithm looking for peak lung inflation becoming active. This delay ensures that the capacitors are fully charged and able to fire the x-ray when the algorithm detects peak inflation. Without the delay, the peak inflation might occur $\frac{1}{100}$ of a second after rotor-up causing the fire button to fire without an x-ray being taken because of insufficient charging of the capacitors. The cord linking the firing handle to the x-ray machine can be, for example, a regular phone cord used to link a phone set to a hand set. The cord should be at least 10 feet long and can be coiled like a telephone cord.

Figure 4:
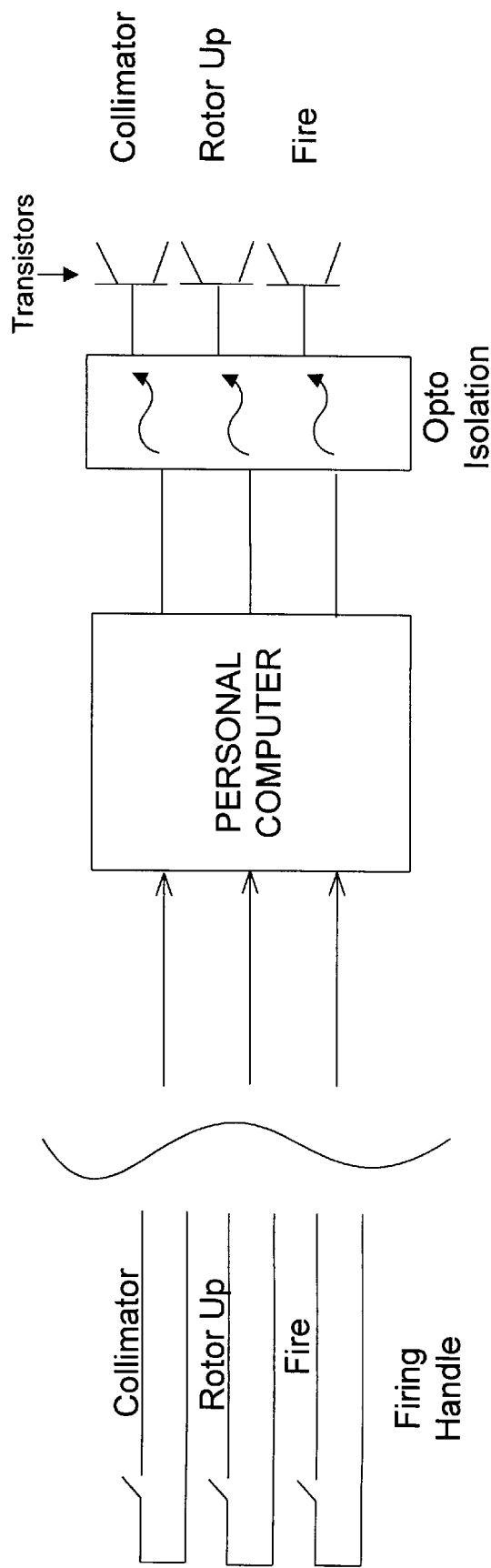
FIG. 4 shows schematically an embodiment of a computer user interface in accordance with the subject invention.

In a preferred embodiment of the subject invention, the functionality of the x-ray trigger handle can be emulated by software. FIG. 4 shows schematically an embodiment of a computer user interface in accordance with the subject invention. Referring to FIG. 4, the three switches in the firing handle, collimator, rotor up, and fire, can each be connected to a bit on a parallel port. By monitoring the status of each switch, the inputs from a user can be implemented, transparent to the user. The status of each bit will change from high to low, or vice versa, depending on the logic, as each switch is opened or closed, on the firing handle. The software can also have a monitoring section on its graphical user interface to determine which buttons have been pressed by the user on the firing handle.

Figure 5:
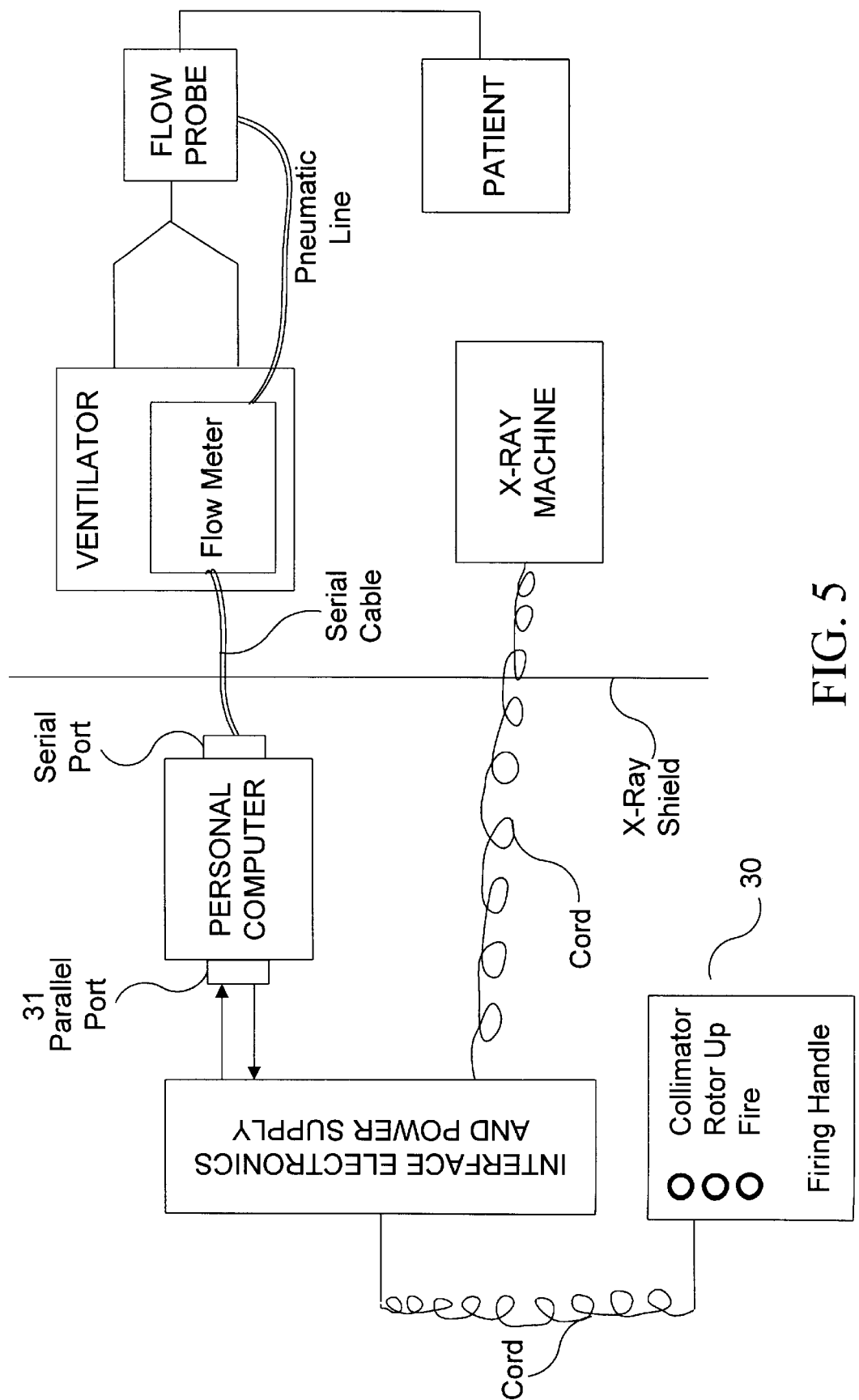
FIG. 5 shows a block diagram of an embodiment of an x-ray trigger emulator in accordance with the subject invention.

FIG. 5 shows a block diagram of a specific embodiment of an x-ray trigger emulator. Referring to FIG. 5, when the user presses the collimator switch, the software can sense the action and instantaneously turn on a transistor which turns on the collimator light. When the user presses the rotor up switch, the button on the PC display can indicate that the user has pressed the rotor up switch and the transistor controlling the rotor-up switch can close instantaneously to start the charging of the capacitors. A two second timer can start counting down. The actual delay will depend on how long the capacitors supplying the x-ray tube take to charge up, in this case two seconds. If a peak lung inflation occurs during the delay period and the user has pressed the "fire" button, nothing will happen until the next full lung inflation. Presumably, this next peak inflation will occur after the delay has elapsed. When the collimator switch is pressed by the user, the button on the PC display representing the collimator switch, can reverse sides or change color to indicate that the collimator switch has been triggered. A window on the PC display that shows the elapsed time in the time delay may also be useful as it would enable the user to know that the delay has not fully elapsed and therefore the system will not fire.

When the user presses the "fire" switch, the software can check to see if the time delay has elapsed. Accordingly, if the time delay has not elapsed, the "fire" transistor is not closed even if a peak lung inflation is detected. Upon the user pressing the "fire" button, on the handle, the button representing "fire" on the PC display, for example, changes color, acknowledging that the request to fire the x-ray has been received and is being processed. If the time delay has elapsed, meaning that the capacitors are charged, the transistor representing the "fire" button can be closed at the next full lung inflation. A buzzer can sound to indicate that the x-ray has been fired and the color of the "fire" button can change to yet another color to indicate the x-ray has been fired. FIG. 6 illustrates one example of a screen design for a PC, according to the subject invention.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A device for improving the efficacy of the taking of a chest image, comprising:
    a means for receiving a signal which indicates a degree of insufflation of a patient; and
    a means for effecting the taking of a chest image with respect to said patient based on said degree of insufflation,
    wherein said device improves the efficacy of the taking of a chest image by coordinating the taking of a chest image with the patient's degree of insufflation.
    wherein said means for effecting the taking of a chest image causes said chest image to be taken when said signal indicates a desired degree of insufflation,
    wherein said signal which indicates the degree of insufflation of a patient is received from a ventilator, wherein the desired degree of insufflation is not minimum insufflation or maximum insufflation.

2. The device according to claim 1, wherein said signal which indicates a degree of insufflation of a patient further indicates the point in the breathing cycle of said patient.

3. The device according to claim 1, further comprising:
    a ventilator model switch comprising settings corresponding to specific ventilators such that said device can interpret the signal indicating the patient's degree of insufflation received from a selected ventilator.

4. The device according to claim 1, further comprising a switch which indicates the degree of insufflation of the patient at which the taking of a chest image is to be effected.

5. A device for improving the efficacy of the taking of a chest image, comprising:
    a means for receiving a signal which indicates a degree of insufflation of a patient; and
    a means for effecting the taking of a chest image with respect to said patient based on said degree of insufflation,
    wherein said device improves the efficacy of the taking of a chest image by coordinating the taking of a chest image with the patient's degree of insufflation,
    wherein said means for effecting the taking of a chest image causes said chest image to be taken when said signal indicates a desired degree of insufflation,
    wherein said signal which indicates the degree of insufflation of a patient is received from a ventilator,
    further comprising:
    a means for causing said ventilator to ventilate the patient with a sigh breath, wherein said chest image of the patient is taken during the sigh breath.

6. The device for improving the efficacy of the taking of a chest image, comprising:
    a means for receiving a signal which indicates a degree of insufflation of a patient; and
    a means for effecting the taking of a chest image with respect to said patient based on said degree of insufflation,
    wherein said device improves the efficacy of the taking of a chest image by coordinating the taking of a chest image with the patient's degree of insufflation,
    wherein said means for effecting the taking of a chest image causes said chest image to be taken when said signal indicates a desired degree of insufflation such that said chest image is taken at the desired degree of insufflation,
    wherein said device effects the taking of a chest image by sending an output signal to an x-ray machine,
    further comprising:
    a means for emulating an x-ray machine firing handle, said means for emulating an x-ray machine firing handle comprising a means for selecting a fire command, wherein a caregiver can select the fire command such that, after a predetermined delay period, said device will send the output signal to the x-ray machine when said signal indicates the desired degree of insufflation.

7. The device according to claim 6, wherein said means for emulating an x-ray machine firing handle comprises a computer interface.

8. The device according to claim 7, wherein the computer interface comprises a button wherein when a caregiver selects the fire command the button on the computer interface indicates the fire command has been received.

9. The device according to claim 6, wherein said predetermined delay period is related to a time period required to charge up at least one capacitor, wherein said at least one capacitor supplies the charge needed to effect the taking of the x-ray image.

10. The device according to claim 6, wherein said predetermined delay period is at least two seconds.

11. The device according to claim 6, wherein said means for emulating an x-ray machine firing handle comprises a means for selecting a collimator command, wherein when a caregiver selects the collimator command a collimator light is turned on.

12. The device according to claim 6, wherein the means for selecting a fire command is a fire button wherein a caregiver can select the fire command by pushing and releasing the fire button.

13. A device for improving the efficacy of the taking of a chest image, comprising:
    a means for receiving a signal which indicates a degree of insufflation of a patient; and
    a means for effecting the taking of a chest image with respect to said patient based on said degree of insufflation, wherein said device improves the efficacy of the taking of a chest image by coordinating the taking of a chest image with the patient's degree of insufflation, wherein said means for effecting the taking of a chest image causes said chest image to be taken when said signal indicates a desired degree of insufflation such that said chest image is taken at the desired degree of insufflation, wherein said device effects the taking of a chest image by sending an output signal to an x-ray machine, wherein said device sends the output signal to the x-ray machine when said signal indicates the desired degree of insufflation, wherein said signal which indicates the degree of insufflation of a patient is received from a flowmeter.

14. The device according to claim 13, wherein said device further comprises an obstructive type flowmeter which generates said signal which indicates a degree of insufflation of a patient.

15. The device according to claim 14, wherein said flowmeter is an orifice type flowmeter.

16. The device according to claim 15, wherein the flowmeter is placed at a Y-piece of the patient.

17. The device according to claim 15, wherein the flowmeter is placed inside a ventilator.

18. A method for imaging a chest of a patient, comprising the steps of:

(a) monitoring a signal outputted from a patient's ventilator, wherein said signal indicates the patient's degree of insufflation;

(b) receiving an indication from a caregiver to effect the taking of an x-ray image; and (c) sending an output signal to an x-ray machine to effect the taking of an x-ray image of the patient when said signal indicates a desired degree of insufflation such that the x-ray image of the patient is taken at the desired degree of insufflation, wherein the x-ray image is taken only after receipt of said indication from the caregiver to effect an x-ray image and the signal indicates the desired degree of insufflation, wherein the caregiver indicates to effect the taking of an x-ray image by selecting a fire command on a user interface.

19. The method according to claim 18, wherein said desired degree of insufflation is peak insufflation.

20. The method according to claim 18, wherein said caregiver indicates to effect the taking of an x-ray image by interfacing with a device which monitors said signal outputted from the patient's ventilator and sends said output signal.

21. The method according to claim 20, wherein said device is electrically isolated from said x-ray machine.

22. A device for improving the efficacy of the taking of a chest image, comprising:

a means for receiving a signal which indicates a degree of insufflation of a patient; and a means for effecting the taking of a chest image with respect to said patient based on said degree of insufflation, wherein said device improves the efficacy of the taking of a chest image by coordinating the taking of a chest image with the patient's degree of insufflation, wherein said means for effecting the taking of a chest image causes said chest image to be taken at a desired degree of insufflation such that said chest image is taken at the desired degree of insufflation, wherein said device effects the taking of a chest image by sending an output signal to an x-ray machine, further comprising:

a means for emulating an x-ray machine firing handle, wherein a caregiver can select a fire command such that, after a predetermined delay period, said device will send the output signal to the x-ray machine when said signal indicates the desired degree of insufflation, wherein a caregiver can select a rotor-up command which initiates the charging of the x-ray machine's capacitor to prepare for firing, and wherein when the caregiver selects the fire command after selection of the rotor-up command the predetermined delay period is measured from selection of the rotor-up command such that, after the predetermined delay period, said device will send the output signal to the x-ray machine when said signal indicates the desired degree of insufflation.

23. A device for improving the efficacy of the taking of a chest image, comprising:

a means for receiving a signal which indicates a degree of insufflation of a patient; and a means for effecting the taking of a chest image with respect to said patient based on said degree of insufflation, wherein said device improves the efficacy of the taking of a chest image by coordinating the taking of a chest image with the patient's degree of insufflation, wherein said means for effecting the taking of a chest image causes said chest image to be taken when said signal indicates a desired degree of insufflation such that said chest image is taken at the desired degree of insufflation, wherein said device effects the taking of a chest image by sending an output signal to an x-ray machine, further comprising:

a user interface, wherein a caregiver can select a fire command such that, after a predetermined delay period, said device will effect the taking of a chest image when said signal indicates the desired degree of insufflation by sending the output signal to the x-ray machine when said signal indicates the desired degree of insufflation.

* * * * *

UNITED STATES PATENT AND TRADEMARK OFFICE
CERTIFICATE OF CORRECTION

PATENT NO.    : 6,370,419 B2
DATED         : April 9, 2002
INVENTOR(S)   : Samsun Lampotang and Paul B. Langevin It is certified that error appears in the above-identified patent and that said Letters Patent is hereby corrected as shown below:

Column 2,
Line 56, "Description" should read -- Disclosure --.

Column 7,
Line 38, "patient's degree of insufflation." should read -- patient's degree of insufflation, --.

Column 8,
Line 11, "The device" should read -- A device --.

Signed and Sealed this

Thirtieth Day of July, 2002

Attest:

Attesting Officer

JAMES E. ROGAN
Director of the United States Patent and Trademark Office